(12) United States Patent
Levine et al.

(10) Patent No.: US 7,955,247 B2
(45) Date of Patent: Jun. 7, 2011

(54) SYSTEMS FOR AND METHODS OF REPAIR OF ATRIOVENTRICULAR VALVE REGURGITATION AND REVERSING VENTRICULAR REMODELING

(75) Inventors: Robert A. Levine, Brookline, MA (US); Judy W. Hung, Newtonville, MA (US); J. Luis Guerrero, Norton, MA (US); Gus J. Vlahakes, Weston, MA (US)

(73) Assignee: The General Hospital Corporation, Boston, MA (US)

(*) Notice: Subject to any disclaimer, the term of this patent is extended or adjusted under 35 U.S.C. 154(b) by 1521 days.

(21) Appl. No.: 10/519,585

(22) PCT Filed: Jun. 27, 2003

(86) PCT No.: PCT/US03/20450
§ 371 (c)(1),
(2), (4) Date: Jan. 9, 2006

(87) PCT Pub. No.: WO2004/002364
PCT Pub. Date: Jan. 8, 2004

(65) Prior Publication Data
US 2006/0129025 A1    Jun. 15, 2006

Related U.S. Application Data

(60) Provisional application No. 60/392,332, filed on Jun. 27, 2002.

(51) Int. Cl.
*A61N 1/362* (2006.01)

(52) U.S. Cl. .......................................... 600/16; 623/3.1

(58) Field of Classification Search .................. 600/37, 600/16–18; 128/897–899; 601/11; 623/3.1, 623/14.13, 23.72
See application file for complete search history.

(56) References Cited

U.S. PATENT DOCUMENTS

| | | | |
|---|---|---|---|
| 6,129,758 A | 10/2000 | Love | |
| 6,165,183 A | 12/2000 | Kuehn et al. | |
| 6,269,819 B1 | 8/2001 | Oz et al. | |
| 6,312,447 B1 | 11/2001 | Grimes | |
| 6,355,030 B1 | 3/2002 | Aldrich | |
| 6,360,749 B1 | 3/2002 | Jayaraman | |
| 6,402,679 B1 | 6/2002 | Mortier et al. | |
| 6,432,039 B1 | 8/2002 | Wardle | |
| 6,461,366 B1 | 10/2002 | Seguin | |

(Continued)

FOREIGN PATENT DOCUMENTS

WO            9635469            11/1996

(Continued)

OTHER PUBLICATIONS

Robert A. Levine et al., "Ischemic Mitral Regurgitation on the Threshold of a Solution from Paradoxes to Unifying Concepts", Contemporary Reviews in Cardiovascular Medicine, 2005; 112, pp. 745-758.

(Continued)

*Primary Examiner* — John P Lacyk
(74) *Attorney, Agent, or Firm* — Dorsey & Whitney LLP

(57) ABSTRACT

Methods of and devices for restoring the normal geometry of a heart, including but not limited to the structures supporting the atrioventricular valves. The techniques and devices described herein operate on the principle of displacement, both active and passive, to reverse cardiac remodeling and limit ischemic atrioventricular valve regurgitation.

22 Claims, 16 Drawing Sheets

U.S. PATENT DOCUMENTS

| | | | |
|---|---|---|---|
| 6,540,666 B1 | 4/2003 | Chekanov | |
| 6,575,971 B2 | 6/2003 | Hauck et al. | |
| 6,626,930 B1 | 9/2003 | Allen et al. | |
| 6,629,534 B1 | 10/2003 | St. Goar et al. | |
| 6,695,866 B1 | 2/2004 | Kuehn et al. | |
| 6,752,813 B2 | 6/2004 | Goldfarb et al. | |
| 6,770,083 B2 | 8/2004 | Seguin | |
| 7,311,731 B2 * | 12/2007 | Lesniak et al. | 623/3.1 |
| 2002/0013571 A1 | 1/2002 | Goldfarb et al. | |
| 2002/0029060 A1 | 3/2002 | Hogendijk | |
| 2002/0161378 A1 | 10/2002 | Dowing | |
| 2003/0120341 A1 | 6/2003 | Shennib et al. | |
| 2005/0003010 A1 * | 1/2005 | Cohen et al. | 424/486 |
| 2008/0065048 A1 * | 3/2008 | Sabbah et al. | 604/511 |
| 2010/0087917 A1 * | 4/2010 | Macha | 623/2.1 |

FOREIGN PATENT DOCUMENTS

| | | |
|---|---|---|
| WO | WO-98/55165 | 12/1998 |
| WO | 9913777 | 3/1999 |
| WO | WO-00/36995 | 6/2000 |
| WO | 0060995 | 10/2000 |
| WO | 0128432 | 4/2001 |
| WO | 2004012583 | 2/2004 |
| WO | 2004014282 | 2/2004 |

OTHER PUBLICATIONS

Judy Hung et al., "Reverse Ventricular Remodeling Reduces Ischemic Mitral Regurgitation Echo-Guided Device Application in the Beating Heart", Circulation, Nov. 12, 2002, pp. 2594-2600.

Judy Hung et al., "Mechanism of Recurrent Ischemic Mitral Regurgitation After Annuloplasty continued LV remodeling as a moving target", Circulation, Sep. 14, 2004, pp. 85-90.

Emmanuel Messas et al., "Chordal Cutting a New Therapeutic Approach for Ischemic Mitral Regurgitation", Ischemic Mitral Regurgitation, Jul. 2001, pp. 1958-1963.

Emmanuel Messas et al., "Efficacy of Chordal Cutting to Relieve Chronic Persistent Ischemic Mitral Regurgitation", Circulation, Sep. 9, 2003, pp. 111-115.

Japanese Office Action dated Jun. 30, 2010 for Japanese patent application No. 2004-518052.

* cited by examiner

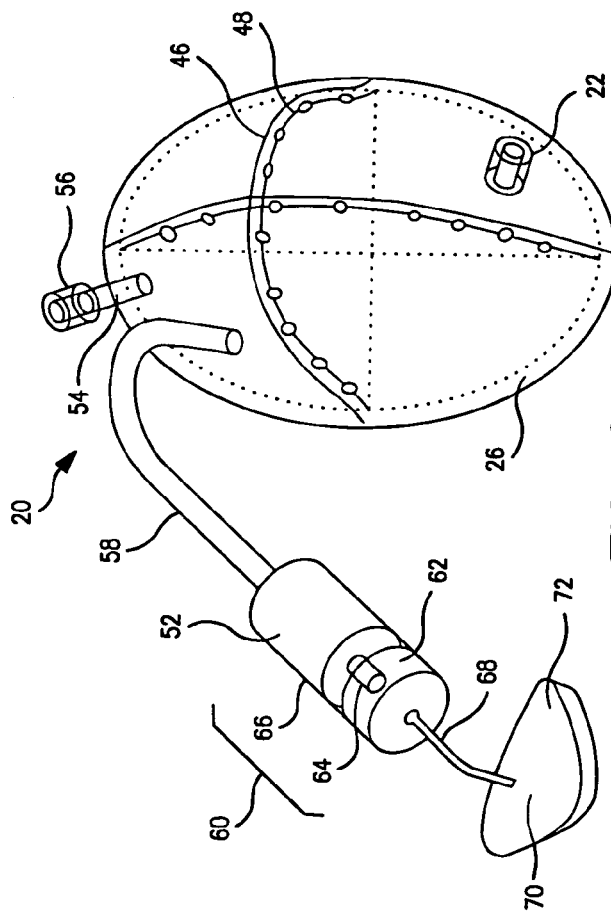
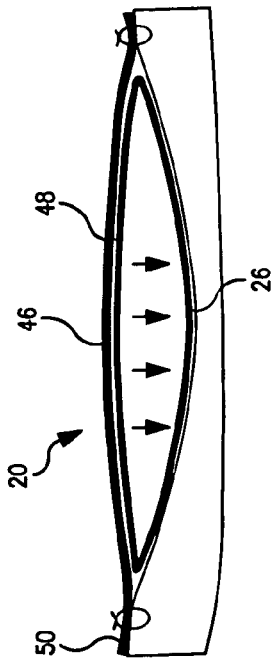
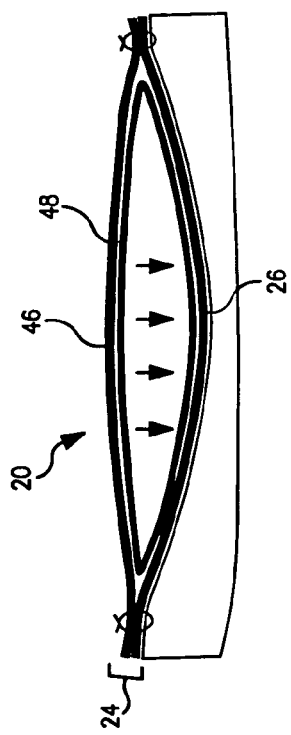
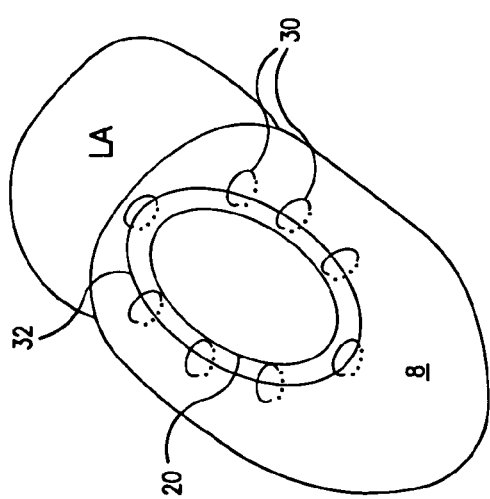

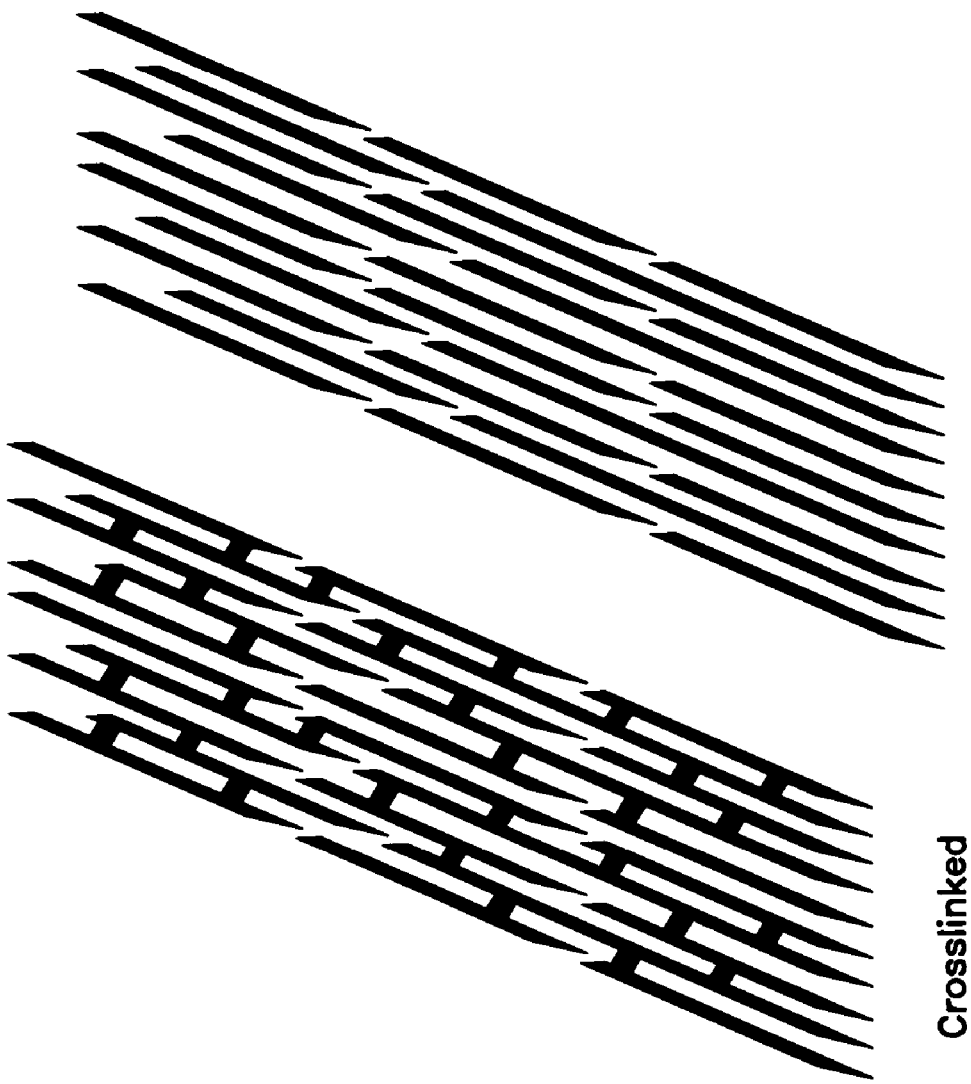

Parallel Polymers

Crosslinked Polymers

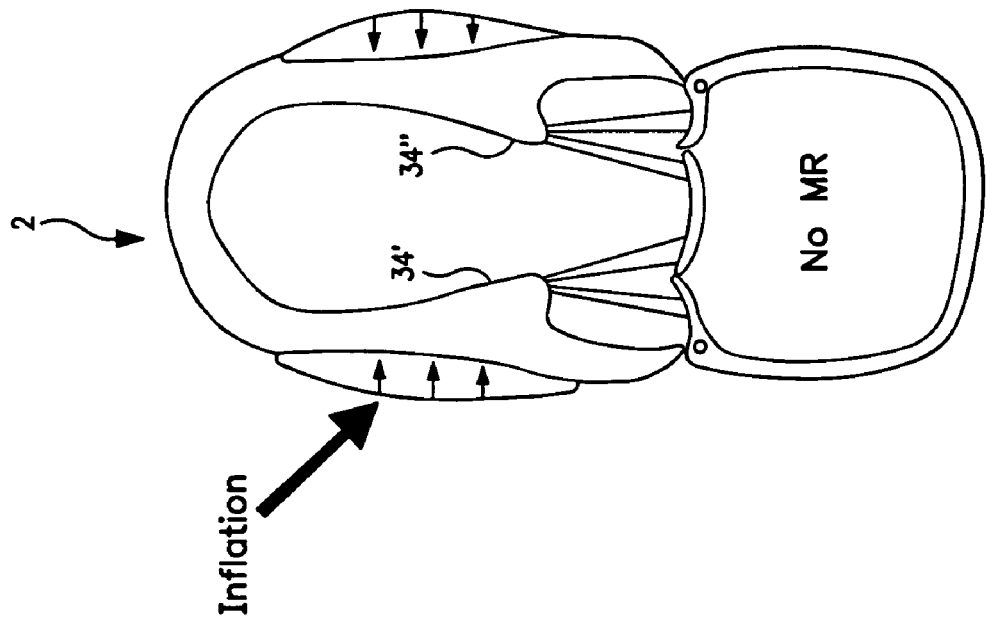
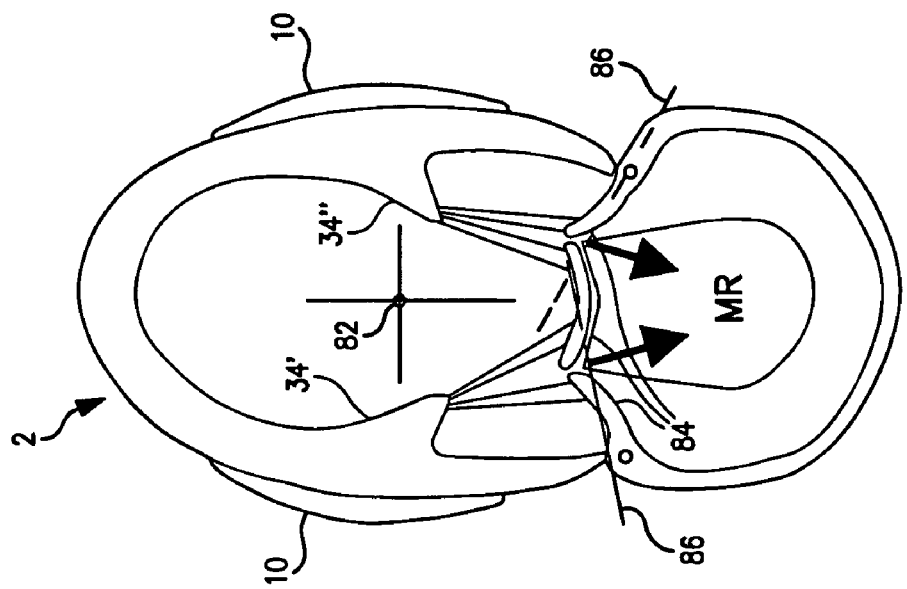
FIG. 8B
FIG. 8A

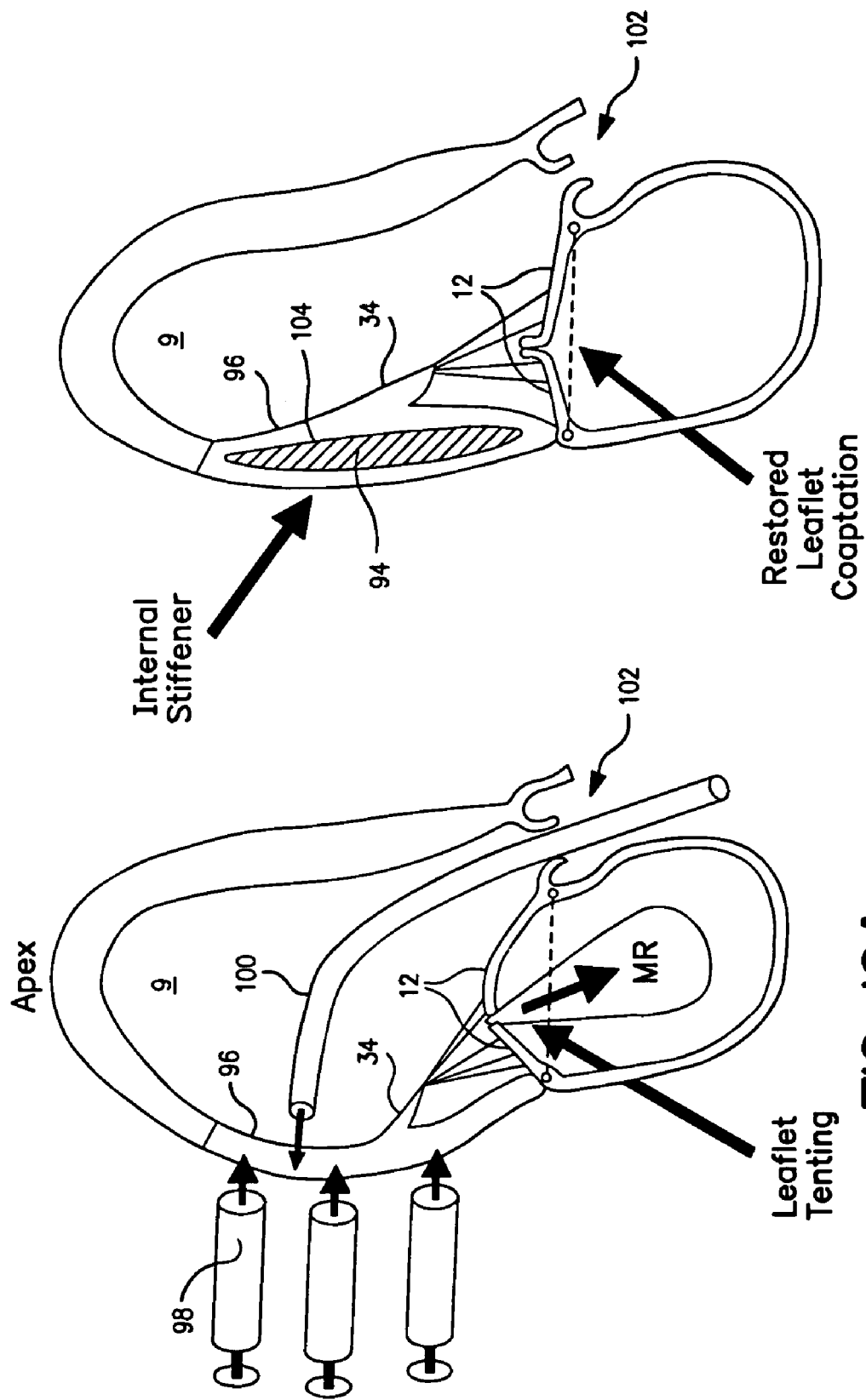

SYSTEMS FOR AND METHODS OF REPAIR OF ATRIOVENTRICULAR VALVE REGURGITATION AND REVERSING VENTRICULAR REMODELING

CROSS-REFERENCE TO RELATED APPLICATIONS

This application claims priority of International Application No. PCT/US2003/020450 filed on Jun. 27, 2003, and U.S. Provisional Application No. 60/392,332 filed on Jun. 27, 2002, the entirety of which are incorporated herein by reference.

FIELD OF THE INVENTION

The present invention relates generally to methods and devices for reversing ventricular remodeling and correcting valvular dysfunction and, more specifically, for locally addressing and reorienting ventricular tissues. Several minimally invasive techniques and adjustable devices are described.

BACKGROUND OF THE INVENTION

Patients with ischemic heart disease experience a wide range of pathological changes. Some of these include ventricular dilatation, dilatation of the mitral annulus, papillary muscle displacement and tethering, papillary infarcts, segmental and global ventricular dysfunction. The mitral valve function and competency rests on the fine geometric and functional integrity of its supporting structures.

When the left ventricle distorts due to dilatation or scarring from myocardial infarction, the papillary muscles are tethered, thus preventing adequate closure of the mitral valve. The left ventricle has two papillary muscles. Both originate from the left ventricular free wall. The anterior papillary muscle is attached to the anterior wall of the left ventricle, close to its lateral border. The posterior papillary muscle originates from the posterior wall, near the junction of the interventricular septum. The mitral valve closure is effected by the apposition of its leaflets. Papillary muscle tethering has been shown to be one of the important mechanisms resulting in mitral valve incompetency, and failure of leaflet apposition. Ischemic mitral regurgitation accounts for significant mortality and morbidity in patients with heart disease (it doubles the late mortality after heart attack and after bypass surgery if unrepaired).

FIG. 1 illustrates the fundamental problem of ventricular dilatation in a heart 2 and its relation to atrioventricular valve regurgitation. (Please note that the view presented is inverted from the normal anatomic presentation, as the heart depicted in this and other figures herein are presented as observed in an ultrasound image, with the apex 4 displayed on top because it is closest to the ultrasound transducer.) A damaged muscular wall 6 of a left ventricle 8, the heart's primary pumping chamber, becomes distorted and bulges outward from the center of the ventricular cavity 9. This displaces the papillary muscle 10, to which mitral valve leaflets 12 are anchored by a network of tendinous chords 14, in turn pulling on the leaflet tips and preventing proper meeting (i.e., coaptation) of the leaflets. This results in improper closure and mitral regurgitation from the left atrium 16 back into the left ventricular cavity 9 across the mitral annulus 18. Such regurgitation can produce heart failure, rhythm disorders, sudden death, and a predisposition to lethal heart valve infections. Even in patients in which ventricular remodeling has not yet resulted in significant atrioventricular valve regurgitation, dilatation causes a greater ventricular cavity volume and a commensurate increase in pumping load on the heart.

Previous work that addressed ischemic mitral regurgitation includes:

(a) Czer et al. documented that revascularization (Coronary Artery Bypass Grafting) alone does not improve mitral regurgitation. In a study of 2000 patients who underwent coronary artery bypass surgery, uncorrected mitral regurgitation nearly doubled the risk of late death.

(b) Mitral valve annuloplasty addresses the mechanism of annular dilation as a cause of ischemic mitral regurgitation. Mitral ring annuloplasty involves sewing a prosthetic mitral ring around the mitral annulus to reduce annular size and force the leaflets of the mitral valve to close better. Clinical observations suggest, however, that it does not always reduce the degree of MR because it does not correct for improper heart geometry. In addition, annuloplasty techniques involve opening the heart, an invasive procedure with significant associated risk, and requires placing the patient on cardiopulmonary bypass (stopping the heart and opening it to insert the ring while using an artificial pump to bypass the heart and lungs). To assess the efficacy of a procedure, one must examine mitral valve function once the heart has been released fully from cardiopulmonary bypass. If the surgical annuloplasty procedure failed to accomplish its objective, then one must reinstitute cardiopulmonary bypass to readjust the ring position. Repetitive cycles of cardiopulmonary bypass increase the already significant morbidity and mortality of surgical mitral ring annuloplasty. Because of these associated risks, surgical mitral ring annuloplasty is often not offered to the sickest patients who might otherwise gain the greatest benefit from the procedure.

(c) Surgical techniques have been advocated for surgically grasping the valve leaflets and stitching them together with a suture or other fastener. There are several difficulties that limit the ability to practice those inventions successfully. In patients with sufficient MR to warrant such procedure, the leaflets are initially misaligned, limiting or precluding the ability of a single device to bring the leaflet tips into juxtaposition in order to suture or fasten them together. Also, in order to be effective, the proposed suction device for grabbing the leaflets must withdraw blood extremely rapidly; unless blood is reinfused immediately, hypotension can ensue. A means for stabilizing the leaflet surfaces must also be utilized, otherwise the suture or staple intended to fasten the leaflets may instead displace them. Also, when the leaflets are overstretched, suturing may not be successful as suturing may increase the tension on the leaflets.

(d) Other ventricular remodeling techniques and patents have been introduced for restraining ventricular size, such as pericardial clamps or harnesses, in some cases having balloons or stakes affixed to them. Such devices encircle the heart in global ventricular dilatation and do not address specific segmental pathology, (i.e., they do not provide selectivity of the target points nor adaptability.) Other devices include passive tensor mechanisms that are inserted through the heart and have as their goal the reduction of ventricle diameter at that point. Permanently implanting components traversing the chambers of the heart is, again, a quite invasive treatment. And these approaches lack precise targeting or sturdy fixation. Rather, such techniques and/or devices have targeted a circumferential change in ventricular geometry versus a specific regional change in displacement, tension, and force. Precise targeting and correction of the stress strain and displacement interactions are specifically important for the intricate geometry of atrioventricular valves.

Thus, what is needed are methods and devices for treating ventricular remodeling and atrioventricular regurgitation by locally addressing the geometric distortion of the supporting structures of the ventricle.

It would additionally be desirable if such a technique could be performed without requiring cardiopulmonary bypass, the need for which frequently influences surgeons not to repair valves, particularly in patients who are more seriously ill and could benefit most from this repair, but are at greatest risk from prolonged bypass.

Further, because damage to heart geometry is also progressive, initial success in reducing regurgitation and/or remodeling is often followed by its recurrence. It would therefore be desirable to employ an approach to addressing these conditions that is adjustable over time.

SUMMARY OF INVENTION

The present invention provides methods of and devices for restoring the normal geometry of a heart, including but not limited to the structures supporting the atrioventricular valves. The techniques and devices described herein operate on the principle of displacement, both active and passive, to reverse cardiac remodeling and limit ischemic atrioventricular valve regurgitation.

Preferred embodiments of the invention include minimally invasive methods (e.g., thoracoscopy) not requiring open-heart surgery or cardiopulmonary bypass. They may be performed in conjunction with or without alternative therapies. More than one location of the heart may be simultaneously treated by the invention.

The present invention allows papillary muscles to be repositioned and thus the normal atrioventricular valve geometry to be restored in order to relieve the tension on the leaflets and allow them to close effectively. It should be noted that, despite the specific embodiments described herein that pertain to mitral valve regurgitation of the left ventricle, the methods and devices described herein are equally applicable to address valve regurgitation on the right side of a heart and dilatation of other heart chambers, and that the term 'papillary muscle', as used herein, means any connecting structure having comparable functionality as the papillary muscle of the left ventricle. Also, use of the 'normalize' with respect to cardiac geometry means moving towards normal and not necessarily complete restoration of normal cardiac geometry. Similarly, certain specific embodiments and descriptions below use the term 'exterior wall segment' to refer to a region of the heart proximate the papillary muscle or extended to the base (i.e., junction of ventricle and atrium), but the term is otherwise not intended to be so limited.

Intraoperative observations suggest that force or pressure applied outside papillary muscle can eliminate atrioventricular valve regurgitation (AVR). The present invention provides devices for placement in a longitudinal plane along a portion of the papillary muscle that exert such forces in three-dimensional space (i.e., causing displacement both normal to and radially from said longitudinal plane.)

The devices for treating AVR generally include a compression member acting on an exterior wall segment of the heart to achieve the displacement of the exterior wall segment inward and toward the center line of the ventricular cavity of the heart so as to normalize papillary muscle geometry and improve leaflet coaptation. In preferred embodiments, the devices are reversibly collapsible or furlable for easier delivery to the heart wall attachment site.

In one embodiment, the displacement is achieved by adjustably inflating an inflatable reservoir disposed between the compression member and a buttressing portion of the device that resists expansion away from the heart, thereby forcing the compression member to move the heart wall segment. The reservoir may also be deflated and re-inflated, either intermittently (e.g., in separate operations at different points of time) or more cyclically, such as in temporal coordination with the electrical activity of the heart. The inflation may be achieved by pumping an inflation fluid or gel from a supply source to the reservoir. Such devices may be atraumatically fastened to the exterior wall by any conventional means, such as suturing to, or beneath, the top layer of the pericardium surrounding the heart.

Echocardiographic imaging may aid in performance of any of the procedural steps described herein, such as guiding the placement of the devices, or monitoring and/or adjusting the displacement of the wall segment the devices effect. Such imaging is also useful in designing the device to have a compressive member contoured to achieve a displacement unique to the portion of the exterior wall segment intended to be displaced.

In another embodiment, the displacement is achieved by filling a fillable region between the compressive member and the buttressing portion with a stuffing. The stuffing may comprise engineered tissue that stiffens in the fillable region (e.g, bone or cartilage forming tissues), thereby maintaining the compressive force on the exterior wall segment. A scaffold structure may be employed to initially receive the engineered tissue. A portion of the apparatus may biodegrade over a time period comparable to that required for the engineered tissue to stiffen to the point of independently providing the displacement force required to move the heart wall segment so as to normalize the papillary muscle geometry and improve leaflet coaptation.

In an alternative embodiment, the engineered tissue includes artificial muscle composed of conducting polymers that actively contract and relax in response to electrical triggering, thereby cyclically moving the exterior wall segment through varying degrees of displacement.

The buttressing portion of the device may comprise a patch or external surface of a pouch, each formed of known biocompatible materials having sufficient stiffness to limit expansion away from the heart as a result of the inflation or filling forces.

The present invention further provides an apparatus and method for reducing regurgitation of an atrioventricular valve of a heart by delivering a material into a muscle wall region of a heart proximate the papillary muscle. The material displaces of a portion of said muscle wall region inward and toward the center line of the ventricular cavity and thus normalizes papillary muscle geometry and improves leaflet coaptation. Suitable materials include hydrogels or nickel titanium alloys (e.g., Nitinol™) that substantially retain their shape after delivery. The material may be encapsulated in a structure implanted within the muscle wall, such as, for example, a balloon or a cellular matrix comprised of fibroblasts.

In one embodiment, the material is injected into the muscle wall region, which may be, for example, the tissue plane between the coronary sinus and mitral annulus in the heart. Alternatively, the region could be a location in the base of the heart.

Artisans will readily appreciate that the devices and methods described above for repositioning papillary muscles to limit AVR may be applied more generally in reversing cardiac remodeling in other heart regions.

BRIEF DESCRIPTION OF THE DRAWING

The advantages of the present invention will be apparent in the following detailed description of the illustrative embodiments thereof, which is to be read in connection with the accompanying drawing, wherein:

FIG. 3 is an illustration of an embodiment of a pouch or patch device in accordance with the present invention;

FIG. 4 is an illustration of an inflatable balloon system in accordance with an embodiment of the present invention;

FIGS. 5A, 5B are cross-sectional view of the plane between an embodiment of the inventive device and an external heart wall;

FIGS. 6A-6E are illustrations of an embodiment of the present invention employing conductive polymers as an active displacement mechanism;

FIGS. 8A-8D are illustrations of cross-sectional and external views of a heart to which are attached multiple inflatable devices;

FIGS. 10A, 10B are illustrations of cross-sectional views of a heart having a wall into which has been delivered an internal stiffening material;

DETAILED DESCRIPTION OF PREFERRED EMBODIMENTS OF THE INVENTION

Figure 2:
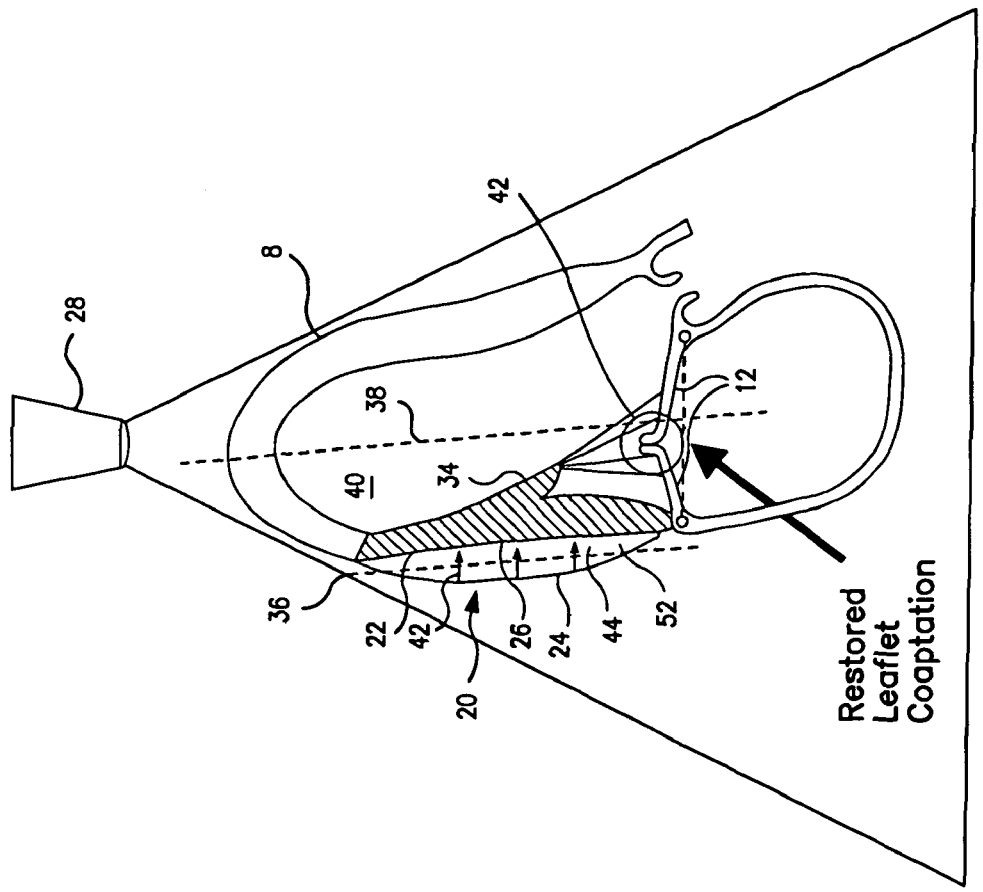
FIG. 2 is an illustration of a cross-sectional view of a heart to which an external pouch has been attached.
Figure 1:
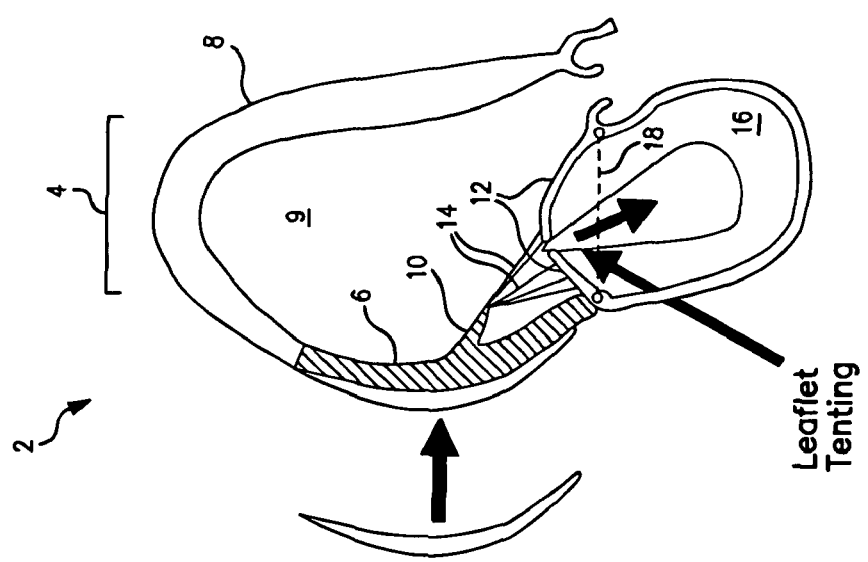
FIG. 1 is a cross-sectional view of a heart exhibiting abnormal mitral valve geometry occurring in ischemic mitral regurgitation.

Preferred embodiments of the present invention will now be described with reference to the several figures of the drawing.

In one embodiment, illustrated in FIG. 2, the present invention provides a device 20 that is secured to an exterior wall segment 22 of the epicardium of a left ventricle 8. Device 20 includes a pouch 24 or a patch (not shown) composed of expanded PTFE or a polyester such as Dacron™ or another known biocompatible material, provided it displays sufficient buttressing properties as described below. Device 20 includes a compression member 26 (e.g., a surface) in contact with exterior wall segment 22. The compression member may comprise a surface of the pouch 24. Alternatively, in patch configurations, the compression member may be an outer surface of an inflatable balloon reservoir. In various embodiments of the present invention described below, the compression member 26 comprises any surface, including non-contiguous surfaces and surfaces defined by engineered cellular material and/or conductive polymers, that serve to deform or move a heart muscle tissue. The surface may additionally be countoured to correspond to the wall segment it is to contact. Prior to implantation, the heart wall may be imaged using an ultrasound transducer 28 in echo cardiography, and a contoured surface may then be pre-formed, for example, through stereolithographic manufacturing.

Device 20 is secured to the exterior wall segment 22 through known means, such as sutures, staples, tined anchors or the like.

FIG. 3 depicts device 20 as an elliptical object lying on the exterior surface of left ventricle 8, fastened by sutures 30. The patch or pouch may have an extended edge 32 or a ring to facilitate placement of sutures. The patch or pouch may also be secured beneath the top layer of the pericardium surrounding the heart.

Returning again to FIG. 2, to treat AVR, device 20 is positioned over a damaged papillary muscle 34. If a discrete infarct exists, it is preferable to cover the region of the infarct (which may be identified by ultrasound), however placement is not limited to damaged or deformed tissue. The long axis 36 of the pouch or patch and compression member 26 is aligned parallel to the centerline 38 of the ventricular cavity 40. The edges of the patch or pouch device 20 are sewn to the heart wall, with care taken to avoid including any coronary blood vessels exposed on this surface. In order to avoid occluding coronary blood flow, one approach that may be taken is to place a semi-rigid protective cover over the coronary artery. Another approach is to not suture the device to the heart wall in that area. The resistance the coronary artery itself provides is sufficient to prevent occlusion. If the heart wall tissue is determined through standard testing to have limited viability, it is obviously less important to avoid possible occlusion than if the heart muscle is viable muscle.

The device also includes a displacement mechanism for moving the compression member 26 inward (in the direction of arrow 42) and toward the centerline 38 of the ventricular cavity 40. The movement of compression member 26 in turn moves papillary muscle 34 into a more normal geometry, and results in an improvement in coaptation 42 between mitral leaflets 12. In the embodiment of FIG. 2, the displacement mechanism comprises an inflatable reservoir 44, such as, but not limited to, a shaped balloon.

FIG. 4 illustrates a preferred embodiment of device 20, which is comprised of an outer Dacron buttressing layer 46, an inner layer comprising compression member 26, and an inflatable reservoir such as balloon 48 serving as a displacement mechanism. FIGS. 5A and 5B present cross-sectional views of alternative embodiments of device 20. In FIG. 5A, inflatable balloon 48 is surrounded by a pouch 24 whose outer surface comprises the buttressing layer 46, and whose inner layer comprises the compression member 26. In FIG. 5B, a surface of the inflatable balloon 48 itself comprises the compression member 26, and the balloon 48 is covered by a patch 50 having a surface comprising the buttressing layer 46.

With reference again to FIG. 4, once device 20 is attached, balloon 48 is filled with an inflation fluid 52 or gel material as described below. The buttressing layer 46 buttresses the structure so that the inflation of balloon 48 preferentially displaces the wall segment of the heart inward toward the centerline of the ventricular cavity (as indicated in FIG. 2.) This result is obtained by designing the buttressing layer 46 to be stiffer than the compression layer 26, through either rigid material selection (e.g., plastics, titanium, stainless) or using more pliable materials having greater widths depending upon their elastic modulus. This repositions the wall segment 22 and papillary muscle 34 toward their normal position, thereby releasing tension on the mitral leaflets 12, which can then meet or coapt more normally without regurgitation. A coapting leaflet surface sufficient to form an effective valve seal is illustrated. The processes of positioning, securing and monitoring displacement can be guided by imaging with ultrasound transducer 28, in order to minimize the amount of inflation fluid 52 or gel required to create the desired repair. Saline, blood or curable polymers are several options for the inflation material, however a large number of biocompatible materials will be understood by artisans to satisfy the inflatabilty requirements of the present invention.

With reference once again to FIG. 4, balloon 48 may include a cannula or access port 54 such as the plastic tube illustrated as leading out of the buttressing layer 46 to a syringe attachment port 56. In another embodiment, a self-sealing silicone rubber port can be utilized, allowing penetration a filling needle that is later withdrawn. For long-term stability of inflatable reservoir size, the syringe port 56 should be locked, or the plastic tube heat-annealed and closed. Other methods for sealing a port are known in the art. In a further embodiment, the cannula or access port 54 is elongated and connected to a sterile subcutaneous port implanted within the chest wall beneath the skin, allowing for subsequent adjustment of inflation material in the reservoir as necessary to maintain valve competence.

The present invention further provides an embodiment (not shown) in which the mechanism for displacing the compression member 26 involves incrementally filling a fill region disposed, again, between a compression member and a buttressing portion with solid or gel material at the time of implantation, and perhaps intermittently thereafter, to achieve the desired reduction of AVR. This may be accomplished by instilling sterile gel into the fill region, using larger ports for the more viscous material, or by stuffing the fill region with layers of expanded PTFE, Dacron™, curable polymers, or other fillers shaped from silicone or other materials. Such fillers may be added between the compression member and buttressing portion, or simply between the buttressing portion (e.g., a patch) and the heart muscle until the desired reduction in regurgitation has been achieved. This may be particularly effective for long-term maintenance.

Advantages of the embodiments of the present invention described above are that they provide direct, targeted repositioning of the positioning of the papillary muscles in a manner completely external to the heart and hence do not require cardiopulmonary bypass or stopping the heart. Unlike other approaches, the present invention can be applied as a surgical option, but does not require excision of myocardium, and thereby the integrity of the muscle layers may be preserved. Devices in accordance with the present invention also allow immediate and/or intermittent adjustment of the papillary muscle repositioning by incrementally varying the displacement of the compression element, through inflation and/or deflation of the inflatable reservoir, or through other filling methods.

In the embodiment illustrated in FIG. 4, the present invention also provides embodiments wherein the displacement of the compression member 26, and thus the segment 22 of the heart muscle wall, is active. Device 20 is made to expand and contract in temporal coordination with the electrical activation of the chambers of the heart, thereby providing the additional benefits of replacing a damaged, non-contracting wall with an active device to augment heart pumping.

One active displacement method involves connecting the inflatable reservoir (e.g., balloon 48) through a plastic tube 58 to an electrically driven pump 60 placed on the surface of the heart or anchored elsewhere within the chest cavity or along the diaphragm or rib surfaces. In simplest form, an electromechanical motor 62 drives a piston 64 to pump inflation fluid 52 from a supply reservoir 66 into the balloon 48, and withdraws the fluid as the heart relaxes. The inflation fluid is preferably relatively non-viscous for efficient pump operation. Pump 60 is triggered by electrical signals recorded by a wire 68, anchored by a tined attachment 70 to the heart wall 72 adjacent the device 20 and amplified for pump triggering. Alternatively, pump 60 can be triggered by a standard transvenous cardiac pacemaker, which senses the cardiac electrical signal and outputs an amplified signal to the pump. Electrical energy for pump operation can be stored in a subcutaneous battery that is re-charged noninvasively using radiofrequency power transmitted through the skin. The tube 58 connecting pump 60 to the inflation reservoir is of larger bore and therefore lower resistance than the smaller access port 54 used to fill the balloon in the static (non-expanding) embodiment.

Figure 6A:
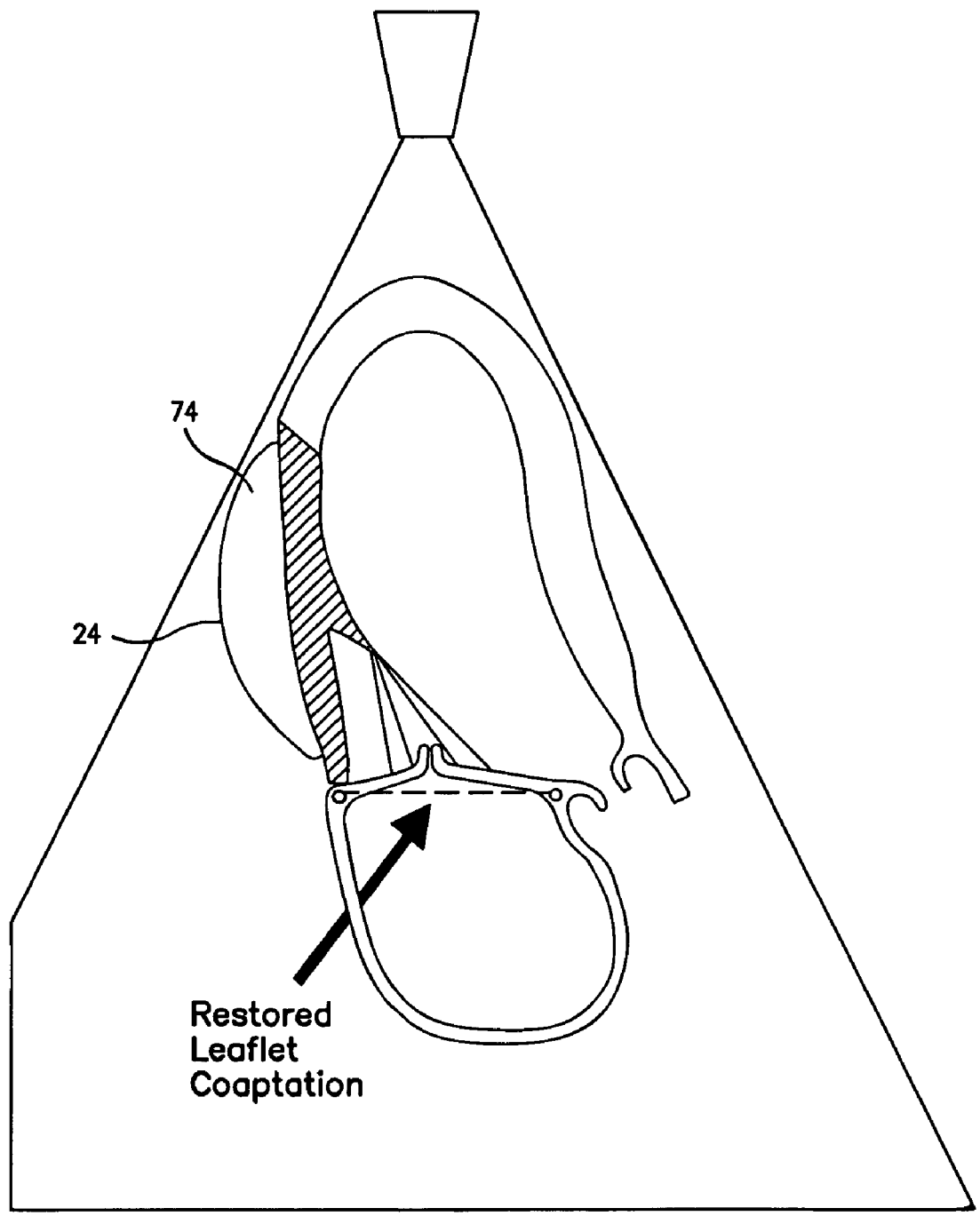
Figure 6E:
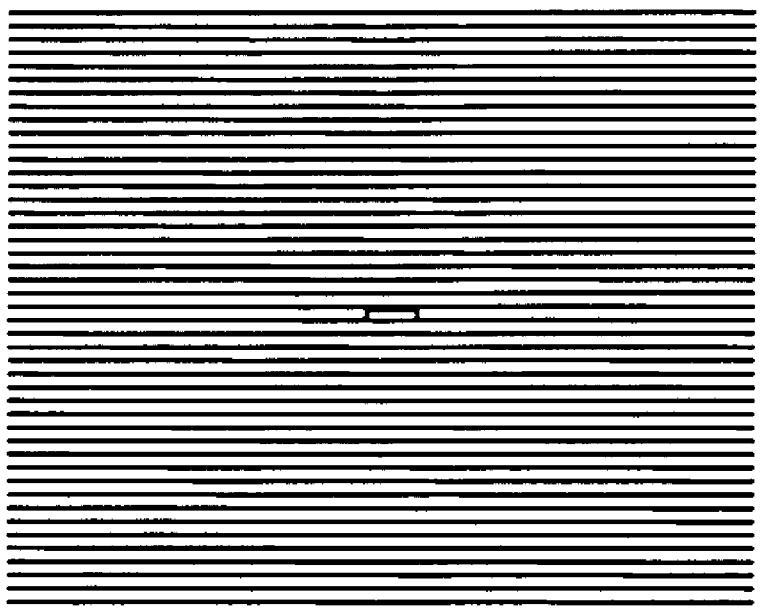
Figure 6D:
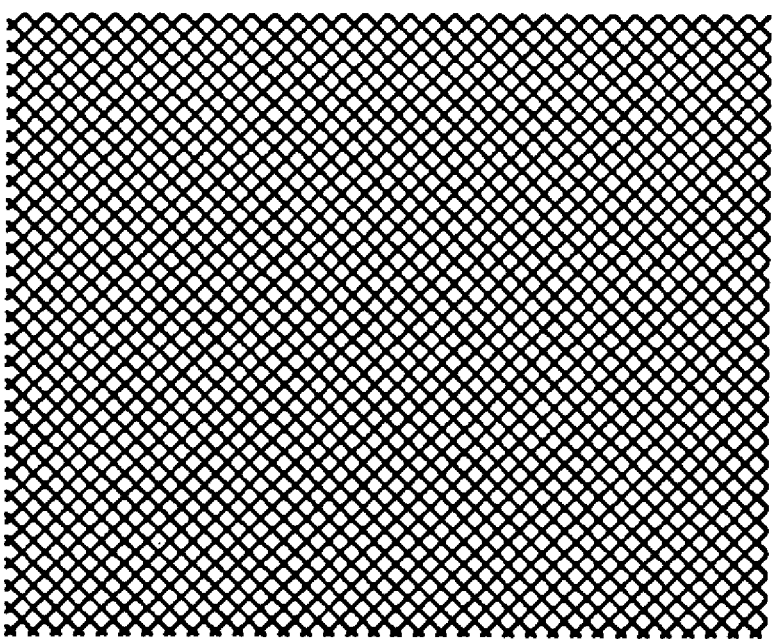

With reference to FIG. 6A, active displacement may alternatively be achieved by use of strips 74 of genetically bioengineered replacement muscle or artificial muscle (cardiomyocyte) in addition to or in lieu of a patch or pouch 24. If the infarct involves and displaces the papillary muscles, an external patch including such artificial muscles will provide the benefit of re-shaping the infarcted wall to relieve AVR, as well as increasing contraction and relaxation to improve overall cardiac function.

Such artificial muscle is made of conducting polymers (such as polypyrrole or polythiophene), repeating pyrrole units that are electrically triggered to contract, for example, over an infarcted region in temporal coordination with the cardiac cycle. FIGS. 6B through 6E illustrate several artificial muscle embodiments comprised of crosslinked and parallel polymer configurations. The conducting polymer strips can change size and shape as current is passed through them, and therefore have the capacity to expand, contract, and generate force. Recent advances have led to swelling pyrrole-based polymers that can achieve tensions of 40 Meganewtons/meter2 (over 250× that of heart muscle), and accordion-like thiophene-based polymers with up to 23% changes in length (comparable to myocardial fiber strain). For a further description of such artificial muscle, see Madden J D, Cush R A, Kanigan T S, Hunter I W. Fast contracting polypyrrole actuators. Synthetic Metals 2000; 113:185-92; Madden J D, Madden P G, Hunter I W. Characterization of polypyrrole actuators: Modeling and performance. Proceedings of SPIE 8th Annual Symposium on Smart Structures and Materials: Electroactive polymer activators and devices. Yoseph Bar-Cohen, ed., SPIE Press 2001; Madden J. Conducting polymer actuators, Doctoral Disseration, Massachusetts Institute of Technology 2000; Marsella M J, Reid R J. Toward molecular muscles: Design and synthesis of an electrically conducting poly {cyclooctatetrrathiophene}. Macromolecules 1999; 32:5982-84; Ding J, Price W E, Ralph S F, Wallace G G. Synthesis and properties of a mechanically strong poly (bithio-phene) composite polymer containing a polyelectrolyte dopant. Synthetic Metals 2000; 110(2): 123-132; and Baughman R H. Conducting polymer artificial muscles. Synthetic Metals 1996; 78:339-353, which are incorporated herein by reference.

Figure 7B:
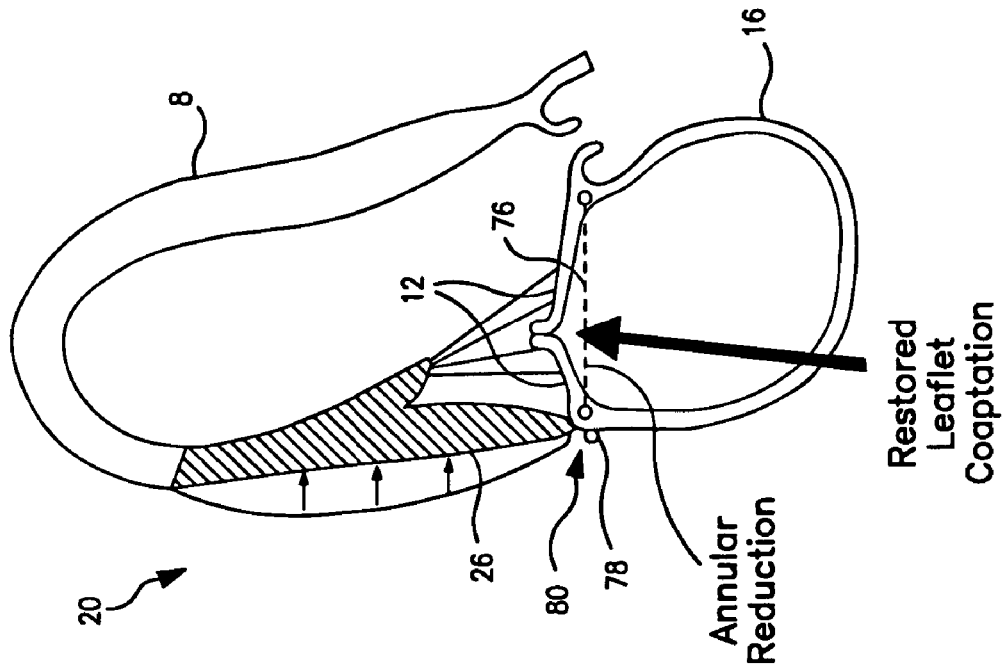
FIGS. 7A, 7B are illustrations of cross-sectional views of a heart to which the device has been attached to additionally address mitral annulus dilatation.
Figure 7A:
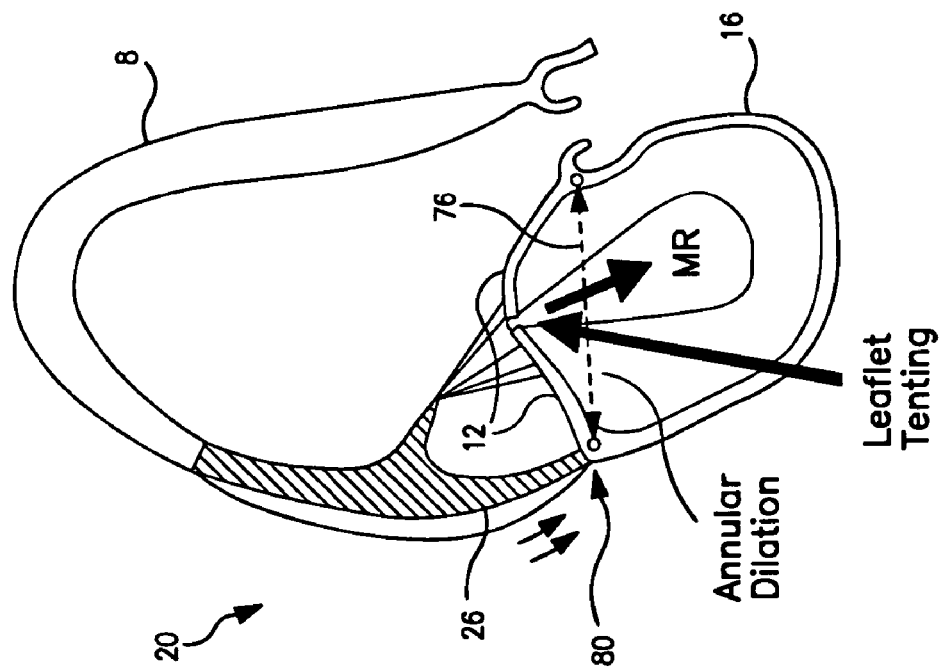

With reference to FIGS. 7A and 7B, ultrasound imaging can assist in recognizing when a mitral annulus 76 is considerably dilated, as indicated in FIG. 7A. In this instance, extension of compression member 26 of device 20 (shown as a pouch) toward the annulus 76 of the valve can reduce annular size as well. Care must be taken to avoid direct pressure on the coronary vessels (such as the coronary sinus 78) in the groove 80 of the heart between left ventricle 8 and left atrium 16. This extension of compressive force towards the base of the heart effectively provides an external annuloplasty or annular size reduction that remedies both ends of the tethering imposed on the mitral leaflets 12 (annular and ventricular). Alternatively, use of the device 20 can be combined with other recently developed approaches for percutaneous annular size reduction. Addition of the pouch can be expected to enhance the efficacy of those other devices. FIG. 7B illustrates a successful reduction in mitral annulus dilatation.

With reference to FIGS. 8A and 8B, the present invention also provides an approach to reversing cardiac remodeling. This embodiment allows application not only to patients with localized heart damage and displacement of an individual papillary muscle (there are two 34', 34"), but also to patients with global dilatation and dysfunction of the left ventricle caused by coronary artery disease or intrinsic disease of the muscle cells (cardiomyopathies causing heart failure.) As shown in FIG. 8A, in such circumstances the heart 2 becomes more spherical than the normal bullet shape, displacing both papillary muscles 34', 34" away from the center of the cavity 82 so that the mitral leaflets 84 are stretched and cannot close, producing regurgitation. (Note that the view shown is a side-to-side ultrasound view through the two papillary muscles 34', 34".) In this embodiment, therefore, devices 20 (e.g., pouches) are placed over both papillary muscles and inflated to reposition those muscles closer to the center of the cavity 82 and to the mitral annulus 86, thereby relieving tension on the leaflets 84 and reducing regurgitation (as reflected in FIG. 8B.) An external view of this embodiment is illustrated in FIG. 8C in the anatomic orientation of the heart (apex down), with two separate pouch devices 20 on the posterior aspect of the heart 2 to displace both of the two papillary muscles.

Figure 8D:
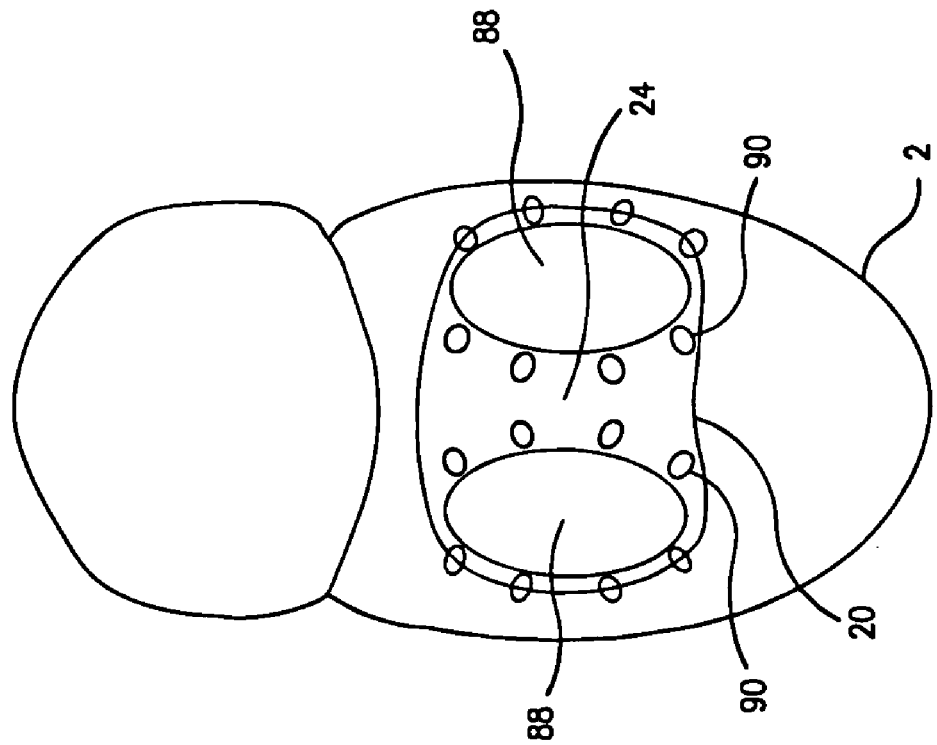
Figure 8C:
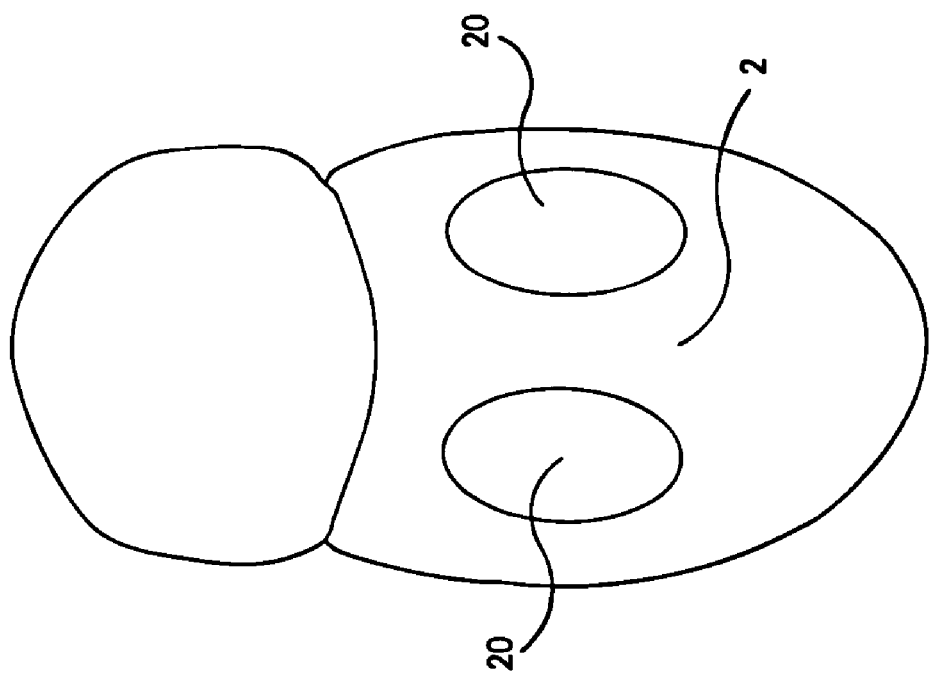

FIG. 8D illustrates an embodiment of device 20 wherein two compressive surfaces, shown as balloons 88, are attached and buttressed by a buttessing layer, shown as a patch or pouch 24. The patch or pouch 24 is sutured to the heart 2 both along its edges and at points 90 encircling the balloons 88. These encircling suture points 90 limit side-to-side expansion of the balloons so that they have the desired effect on the papillary muscles. These embodiments for global dysfunction may also be modified to employ any of the treatment methods described above (i.e., active displacement, extension of compression to the annulus, etc.), alone or in combination.

Any of the device embodiments described herein may be employed in a minimally invasive fashion using thoracoscopy or robotic surgery. In such processes, elongated or tubular viewing and manipulating devices are inserted into the thoracic cavity through one or more small openings in the chest wall. Exemplary devices include videoscopic devices, instruments for pericardial incision and for securing the device to the external heart surface. In these embodiments, the device itself is reversibly collapsible or furlable to allow such introduction, and may be made self-expanding using a variety of mechanisms recognized in the art, such as mounting rings comprised of shape memory materials. This self-expanding technology is known to artisans. Numerous additional embodiments of the device involving variations in the shape, size, and materials of the pouch or patch devices will be readily appreciated by said artisans. For example, rectangular devices may be used, and a range of sizes can be available and selected by the physician to match the size of the damaged or bulging area of heart muscle as displayed by ultrasound or magnetic resonance imaging.

Figure 9B:
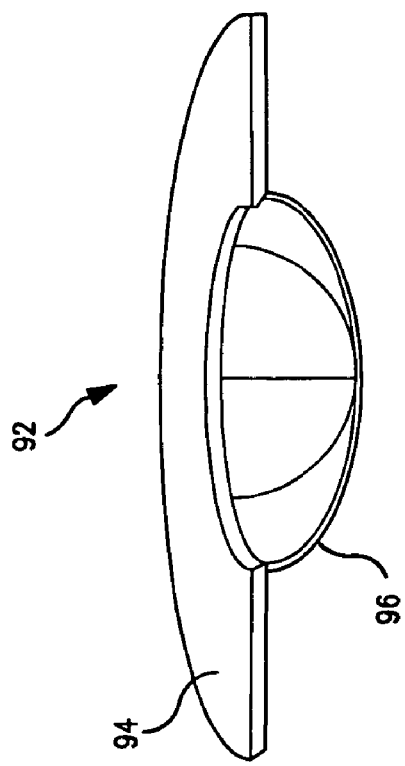
FIGS. 9A-9D are illustrations of deformable devices and cross-sectional views of a heart to which such deformable devices are attached.
Figure 9A:
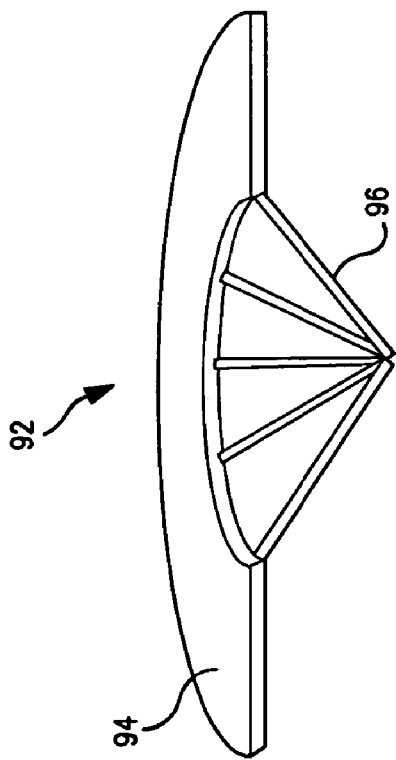
Figure 9D:
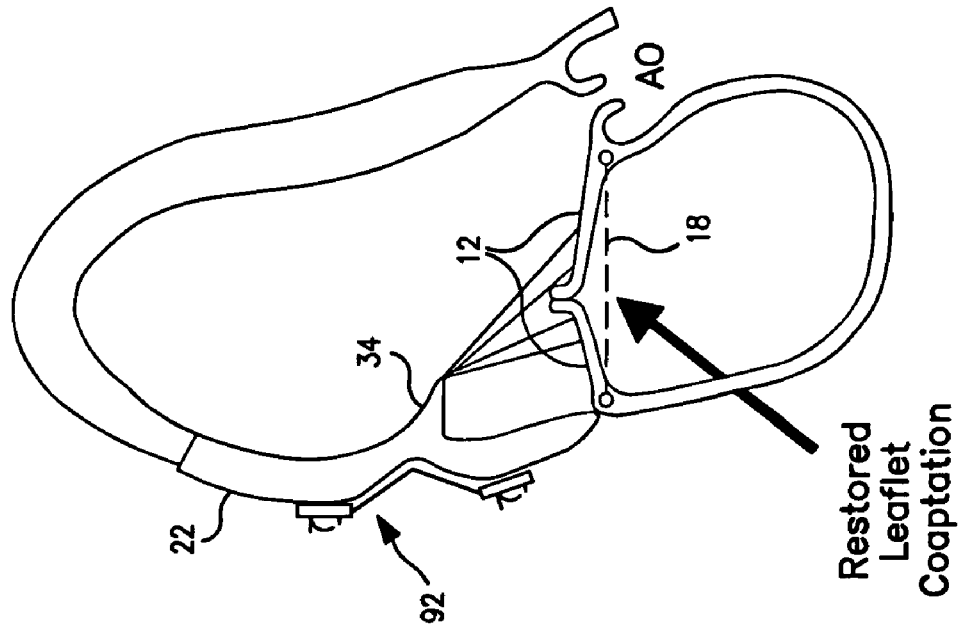
Figure 9C:
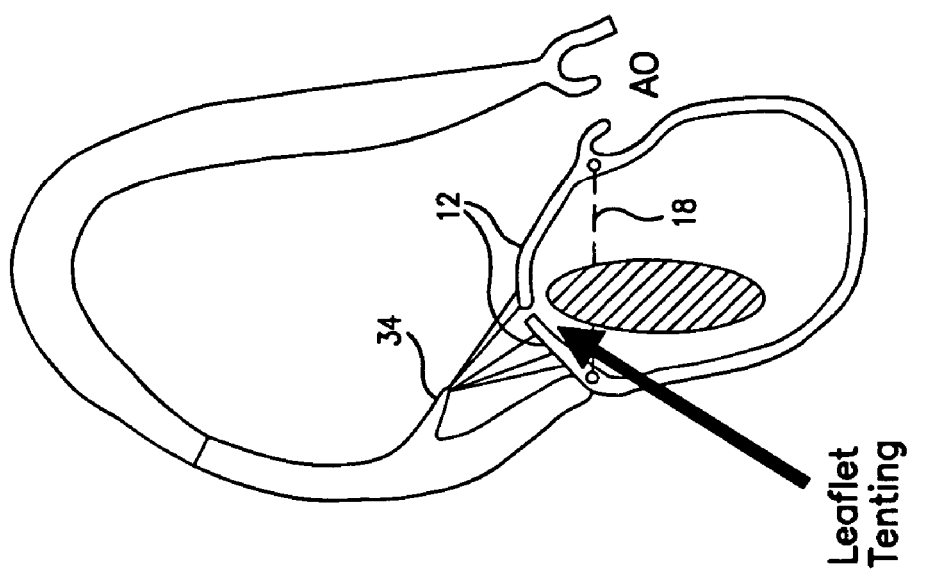

With reference to FIGS. 9A through 9D, in another embodiment, the present invention provides structures, such as springs or hoops, made of shape memory materials, such as super elastic nickel titanium alloy (Nitinol™ www.nitinol.com) may be used to maintain papillary muscle displacement or deformity and to reverse cardiac remodeling. FIGS. 9A and 9B illustrate two versions of such deforming device 92. Device 92 comprises pre-formed or adjustable structures that are affixed to an external surface of the heart so as to reposition the papillary muscle and normalize mitral leaflet coaptation. Device 92 may comprise a mounting ring 94 lying on the heart surface and elements or structures extending below the level of the mounting ring as a continuous or interrupted surface, such as a meshwork or radial spokes. Affixing the ring 94 to the external heart surface 22 forces the protruding elements to displace the papillary muscle, directing it toward the center line of the ventricular cavity (as described above.) The device may also be shaped to direct the papillary muscle 34 toward the base of the heart (the mitral annulus 18) to reduce the tethering applied to the mitral leaflets. Such indenting or repositioning devices may be comprised of fixed or shape memory materials such as nickel titanium alloy. Devices of different size and shape may be available to provide different degrees of repositioning, which can be estimated through echocardiographic imaging as the device or a surgeon's finger is placed to exert pressure against the heart wall.

With reference to FIGS. 10A and 10B, the present invention further provides a method and apparatus for reducing AVR involving delivery of an internal stiffener 94 serving as a buttress into a muscle wall 96. A damaged heart wall typically becomes thinner by virtue of the loss of contracting muscle cells, and bulges outward under the influence of pressure within the ventricular cavity 9. In this embodiment, the internal stiffener 94 comprised of biologically compatible material is delivered (e.g., by syringe 98 injection or implantation) into a region of the damaged heart wall 96, through the exposed external heart wall or by a catheter 100 passing through the aortic valve 102 and guided by electrical sensing or ultrasound imaging to locate the damaged wall. FIG. 10B shows the resulting internal stiffener 94 or buttress to thicken the affected wall 96 and alter its material properties so that its deformation is reduced. This results in reduced mitral leaflet 12 tethering and regurgitation in parallel. This embodiment can be applied both in localized damage involving one papillary muscle and in global dysfunction affecting both muscles. The material injected may include but is not limited to collagen matrix or myoblasts (primitive muscle cells, harvested, for example, from the patient's own skeletal muscle), which have been shown to remain viable even in heart walls with limited blood supply, and may develop contractile capabilities as well.

Such stiffeners may be delivered within a structure, such as a pouch 104 or cellular scaffold, inside the heart wall. The initial structure may be biodegradable, such that the stiffener material has time to stiffen before the structure degrades.

One skilled in the art will also recognize that the techniques and devices described above have the additional advantage of limiting or even reversing the phenomenon of ventricular remodeling. Remodeling is a progressive expansion of a damaged heart affecting both damaged and undamaged walls (for example, walls with and without sufficient blood supply), associated with weakened contraction of the initially undamaged walls. Mitral regurgitation provides a potent stimulus for such remodeling, and reducing such regurgitation using the device of the invention can therefore also limit remodeling. Further, Kelley S T, et al. (Circulation 1999; 99:135-42) have shown that even limiting the expansion of a damaged wall not located near the papillary muscles (and therefore not causing regurgitation) has the added benefit of limiting remodeling and maintaining contractile function of the entire heart. The present invention therefore provides this additional benefit.

Experience of the inventors with the embodiment of the device in FIG. 4 (with or without inner pouch layer) in 10 animals with acute or chronic ischemic mitral regurgitation has shown that the regurgitation could be reversed and eliminated in all instances without adverse effects on left ventricular pump or filling function or pressures. We studies 10 sheep with ischemic MR produced by circumflex ligation with inferior infarction, six acutely and four at 8 weeks post-MI. A Dacron™ pouch containing an inflatable balloon was placed over the papillary muscles and adjusted under echo guidance with the aim of reversing left ventricle remodeling to reposition the infarcted papillary muscle toward the anterior mitral annulus, thereby reducing leaflet tethering and mitral valve regurgitation. 3D echo assessed mitral valve geometric changes, including tethering distance from papillary muscle to anterior annulus. In 7 sheep, sonomicrometry and left ventricular Millar catheters were placed to assess changes in end-systolic and end-diastolic pressure volume relationships (ESPVR and EDPVR), and microspheres injected to assess coronary flow. In all 10 sheep, moderate MR post-MI resolved with pouch application alone (n=3) or echo-guided balloon inflation, which repositioned the infarcted PM toward normal, decreasing the papillary muscle tethering distance from 31.1±2.5 mm post-MI to 26.8±1.8 with pouch (p<0.01 baseline=25.5±1.5). left ventricular contractility was unchanged (ESPVR slope (3.4±1.6 mm Hg/ml with pouch vs 2.8±1.6 post-MI.) Although left ventricular stiffness constant trended higher (0.07±0.05 ml-1 vs 0.05±0.03 post-MI, p=0.06), LVDEP was unchanged as mitral valve regurgitation resolved. Coronary flow to non infarcted regions was not significantly reduced.

An additional 5 animals with chronic ischemic mitral valve regurgitation were followed for 6 to 8 weeks after successful reduction of mitral regurgitation without recurrent leak.

Figure 11:
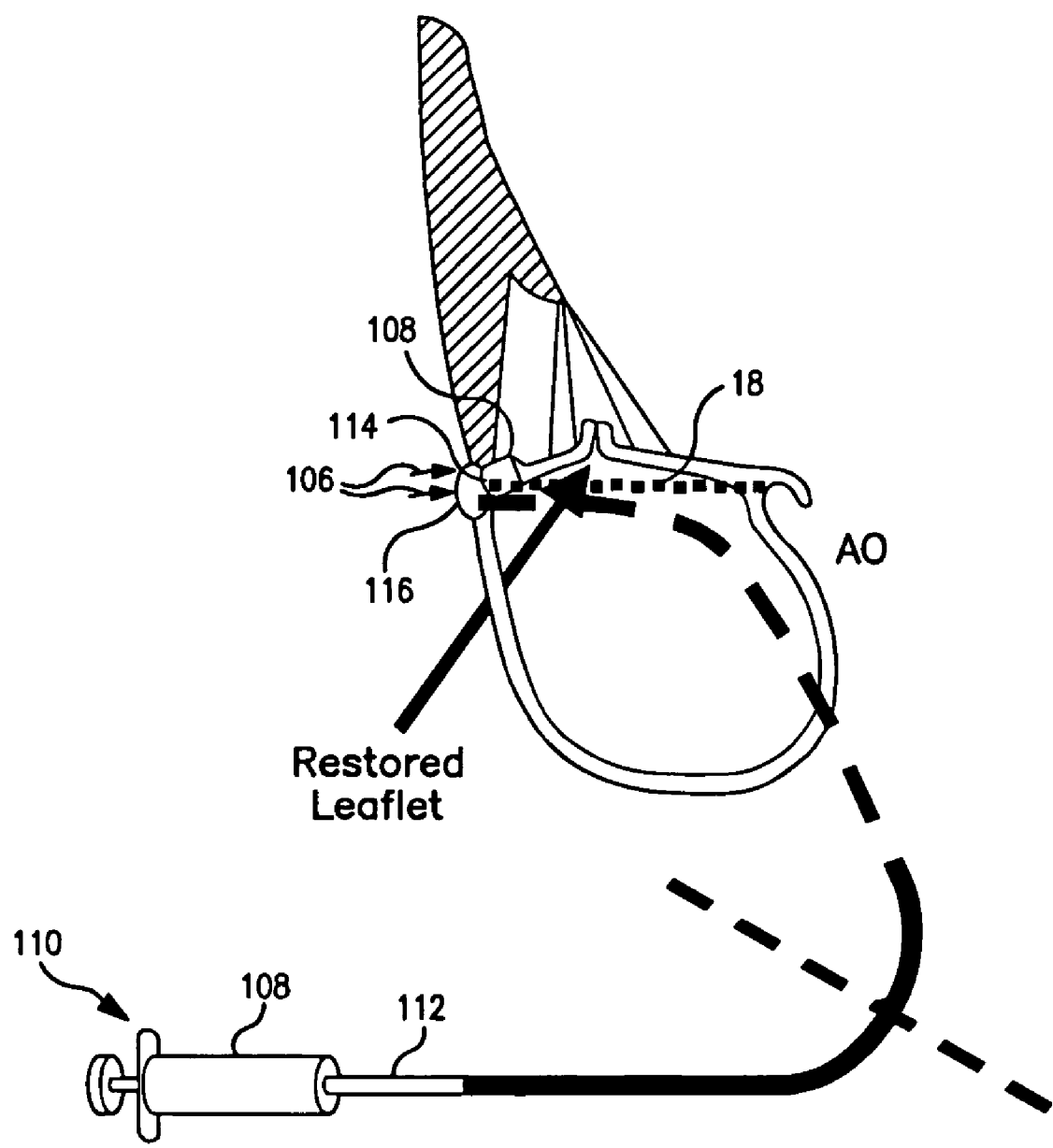
FIG. 11 is an illustration of a heart viewed via an ultrasound image depicting percutaneous delivery of a polymer material and/or encapsulating structure via coronary sinus.

In another embodiment shown in FIG. 11, the present invention provides an apparatus and technique for anteriorly displacing (in the direction indicated by arrows 106) the annulus (dashed lines and 18) using the injectable, space-occupying material 108 injected (e.g., by catheter system 110 through a needle 112) or otherwise inserted through a needle 112 into the tissue plane 114 between the coronary sinus 116 and annulus resulting in anterior displacement of the annulus. Because the coronary sinus 116 is the largest vein of the heart muscle, it is ideally suited for deployment of devices to affect or displace the mitral annulus as it is located immediately adjacent to the mitral annulus and is readily accessible by percutaneous catheter systems 110. Particular advantages to deployment of device through the coronary sinus is the ease of percutaneous access to the coronary sinus which would entail a catheter threaded into the right side of the heart via a peripheral leg or arm vein. This would obviate the need for an open-surgical procedure for delivery of device if material.

Figure 12:
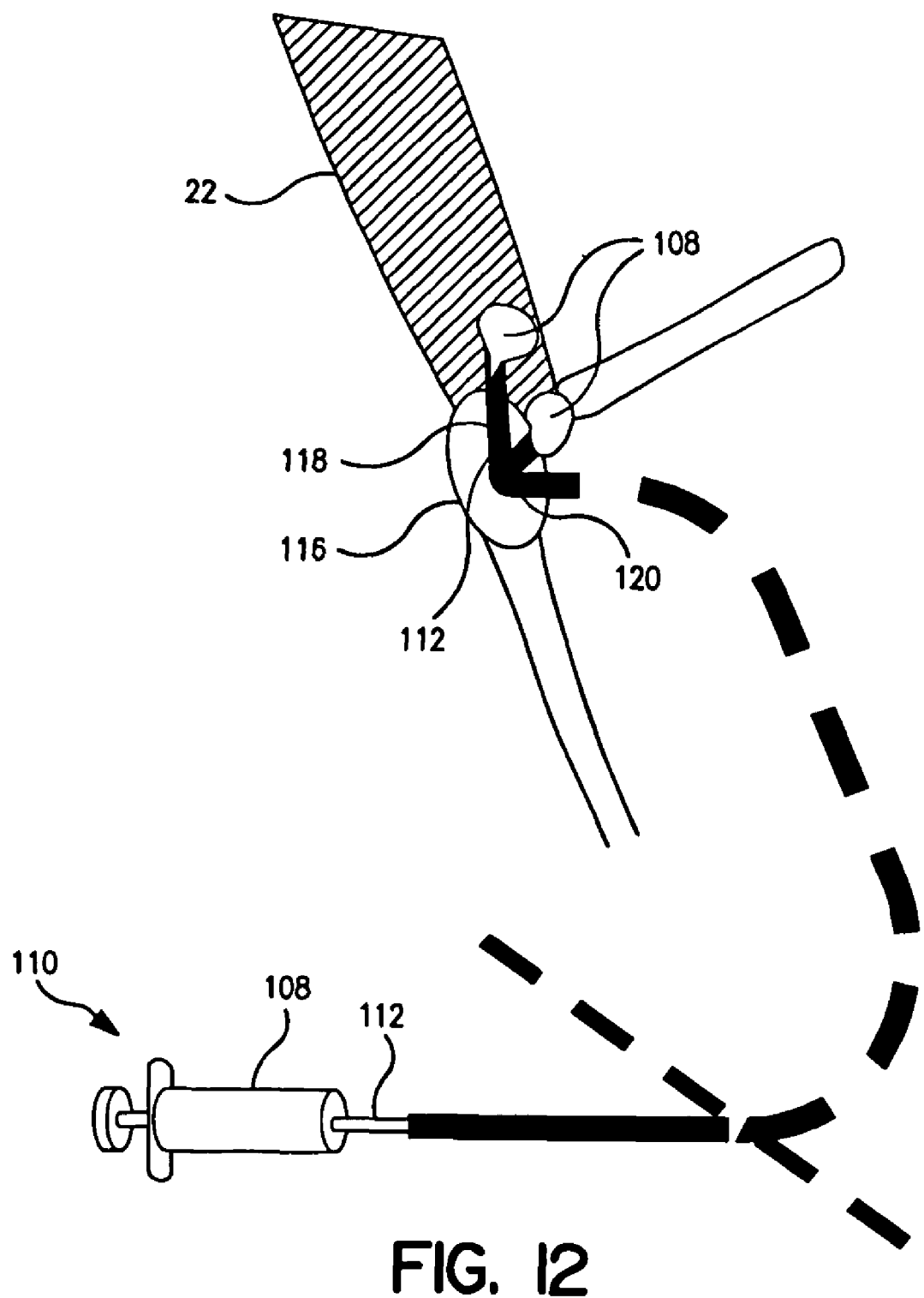
FIG. 12 is an exploded view of the region of the heart proximate to the site(s) of material and/or encapsulating structure delivery via a catheter system.

FIG. 12 is an expanded view of the region of the heart proximate to the injection site(s). Orthogonal injection needle orientations 118, 120 indicate the ability to inject material 108 wherever necessary to effect the desired displacement. This could be directed into the tissue plane between the annulus and coronary sinus or more inferiorly into the base of the heart. The biocompatible material is preferably comprised of a polymer gel or similar material.

As shown in FIG. 11, the resulting displacement of the mitral annulus (dashed lines and 18) anteriorly reduces the overall mitral annular area, restoring mitral leaflet coaptation. Characteristics of the material 108 include flexibility of deformation and physical properties of the material are chosen to withstand the forces normally generated in contracting myocardium such that it would retain its original shape and volume. The material 108 is preferably initially in liquid form and hardens at body temperature and hence injectable through commercially available percutaneous catheter systems such as Transvascular, Inc. (Menlo Park, Calif.) or Bio-Cardia, Inc. (South San Francisco, Calif.). Hydrogels such as alginate polymers are an example of such material. These polymers are biocompatible and biodegradable and can be adapted to be in liquid form at room temperature but solidify at body temperature (for more on these polymers, see Vacanti J P, Langer R. Tissue engineering: the design and fabrication of living replacement devices for surgical reconstruction and transplantation. Lancet. 1999 July; 354 Suppl 1:SI32-4, and Marler J J, Guha A, rowley J, Koka R, Mooney D, Upton J, Vacanti J P. Soft tissue augmentation with injectable alginate and syngeneic fibroblasts. Plastic Reconstrutive Surgery 2000; May; 105(6):2049-58, incorporated herein by reference.) In addition, the firmness of the hydrogel can be adjusted to the degree necessary to withstand the normal loading forces present in the heart.

Figure 13:
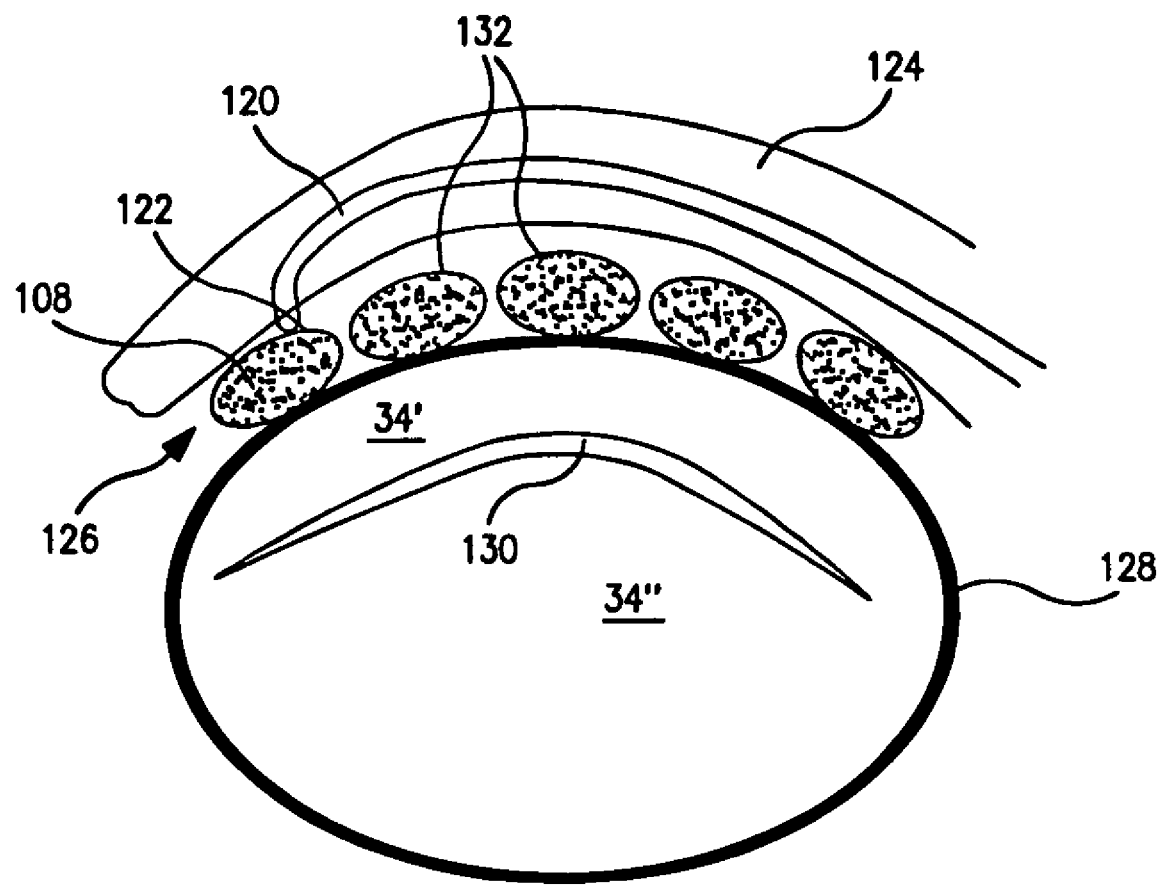
FIG. 13 is an illustration of tissue region receiving injection proximate to coronary sinus and annulus.

With reference to FIG. 13, a catheter 120 with an injection needle 122 is placed into the coronary sinus 124 and aliquot injections 132 of the biomaterial 108 are made, as necessary, into the tissue plane 126 between the coronary sinus 124 and mitral annulus 128 along the length of the mitral annulus through the needle 122. The injections produce anterior or inward displacement of the posterior mitral leaflet 34' towards anterior mitral leaflet 34", restoring proper mitral leaflet coaptation (closure of mitral orifice 130).

Figure 14:
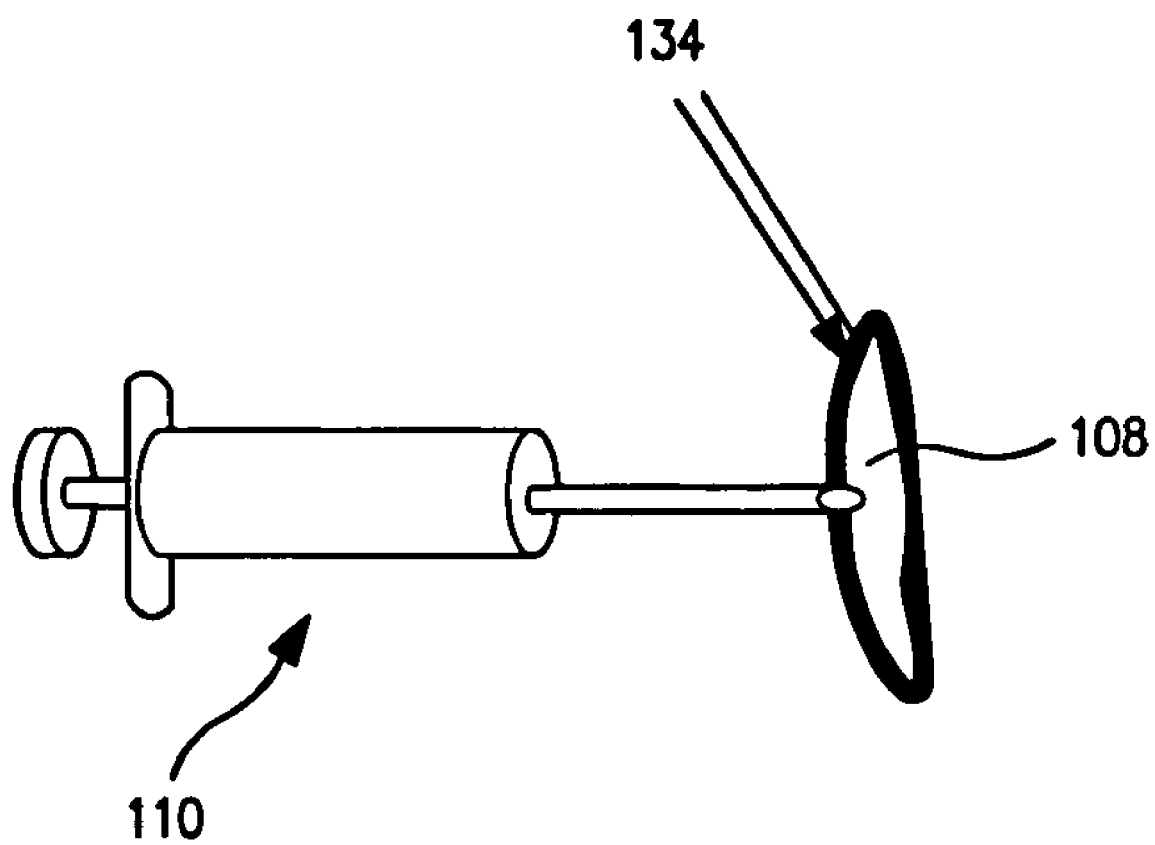
FIG. 14 is an illustration of tissue region receiving injection proximate to coronary sinus and base of the heart.

In another embodiment illustrated in FIG. 14, material 108 is injected within an encapsulating structure 134 or shell, such as a polymeric balloon or a cellular matrix composed of fibroblasts, which would serve to retain the volume and shape of the injected material. Balloon material could be similar to those in artificial urinary sphincters which contain implantable and inflatable balloons or balloon expanders used in plastic reconstructive surgery (for further discussion of these materials, see Wilson T S, Lemack G E, Zimmern P E. Management of intrinsic sphincteric deficiency in women. J Urol. 2003 May; 169(5): 1662-9; Gonzalez R, Schimke C M. Strategies in urological reconstruction in myelomeningocele. Curr Opin Urol. 2002 November; 12(6):485-90; Kabaker S S, Kridel R W, Krugman M E, Swenson R W. Tissue expansion in the treatment of alopecia. Arch Otolaryngol Head Neck Surg. 1986 July; 112(7):720-5. Radovan C. Tissue expansion in soft tissue reconstruction. Plast Reconstr Surg 1984 October; 74(4):482-92; incorporated herein by reference.) In another embodiment, biomaterial could be injected within a fibroblast shell, allowing for retention of volume and shape of injected material.

Figure 15:
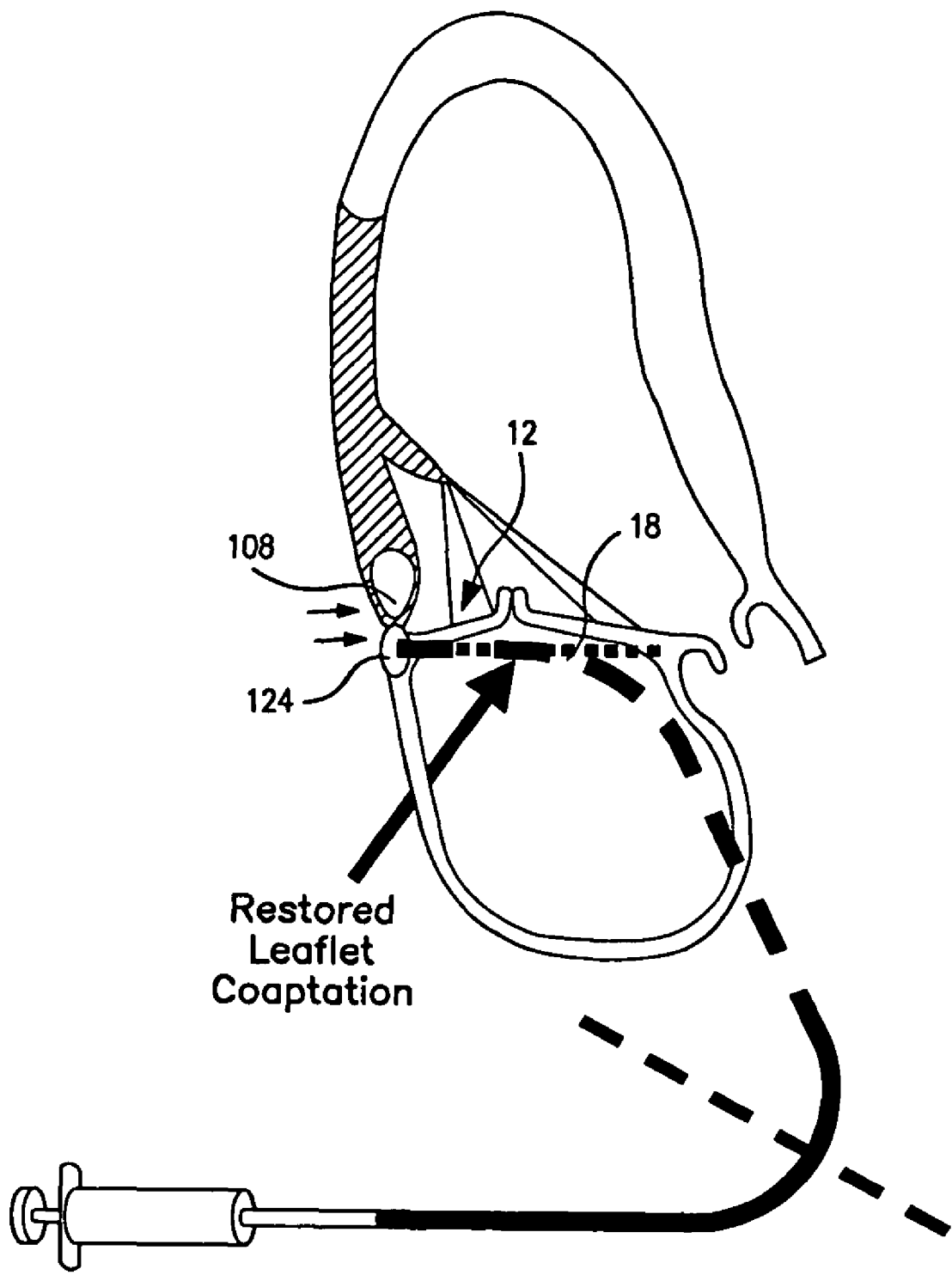
FIG. 15 is an illustration of a catheter system used to inject a biocompatible material within an encapsulating shell.

With reference to FIG. 15, the material 108 can also be injected through a catheter 136 in the coronary sinus 124 inferiorly into the base of the heart (as indicated by needle orientation 118 in FIG. 12), along the length of the mitral annulus 18, resulting in an appropriate displacement of the mitral leaflet 12. Injections into the base of the heart could serve as an adjunct to injections at the annular level or as an independent method to displace the annulus.

In another embodiment, material 108 consists of tissue-engineered material, with an initial scaffolding network. The tissue-engineered material could be adapted or customized to the appropriate physical properties to effect mitral annular displacement. Specifically, tissue-engineered material would consist of patient's own stem cells and programmed to transform into chondrocytes, producing a cartilaginous structure in the desired region (see Yoshimoto H, Shin Y M, Terai H, Vacanti J P. A biodegradable nanofiber scaffold by electro-spinning and its potential for bone tissue engineering. Biomaterials. 2003 May; 24(12):2077-82; Abukawa H, Terai H, Hannouche D, Vacanti J P, Kaban L B, Troulis M J. Formation of a mandibular condyle in vitro by tissue engineering. J Oral Maxillofac Surg. 2003 January; 61(1):94-100; Fuchs J R, Terada S, Hannouche D, Ochoa E R, Vacanti J P, Fauza D O. Engineered fetal cartilage: structural and functional analysis in vitro. J Pediatr Surg. 2002 December; 37(12):1720-5; Young C S, Terada S, Vacanti J P, Honda M, Bartlett J D, Yelick P C. Tissue engineering of complex tooth structures on biodegradable polymer scaffolds. J Dent Res. 2002 October; 81(10):695-700; incorporated herein by reference.) Cartilaginous material would have the desired physical firmness to result in anterior displacement of the annulus as well as ability to withstand the forces present in the heart. Cartilaginous structures are present naturally in the anterior portion of the mitral annulus. Other tissue-engineered material could consist of injection of muscle into the annulus or base of the heart to produce annular displacement (see Saxena A K, Willital G H, Vacanti J P. Vascularized three-dimensional skeletal muscle tissue-engineering. Biomed Mater Eng. 2001; 11(4): 275-81; Saxena A K, Marler J, Benvenuto M, Willital G H, Vacanti J P. Skeletal muscle tissue engineering using isolated myoblasts on synthetic biodegradable polymers: preliminary studies. Tissue Eng. 1999 December; 5(6):525-32; incorporated herein by reference.) An additional advantage of muscle would be the potential to produce dynamic contraction, timed to the cardiac cycle to augment heart function.

Proper localization of the injection(s) may be aided by echocardiography. Additionally, the efficacy of the appropriate posterior mitral annular correction can optionally be monitored and guided noninvasively by real-time echocardiography.

While the foregoing specification has been described with regard to certain preferred embodiments, and many details have been set forth for the purpose of illustration, it will be apparent to those skilled in the art, that without departing from the spirit and scope of the invention, the invention may be subject to various modifications and additional embodiments, and that certain of the details described herein can be varied considerably without departing from the basic principles of the invention. Such modifications and additional embodiments are also intended to fall within the scope and spirit of the invention appended claims.

What is claimed is:

1. A method of reversing cardiac remodeling, comprising: delivering a material through an external tissue portion of the heart and into a region of tissue of the heart so as to displace a portion of the region of tissue inward and toward the center line of the ventricular cavity, thereby normalizing cardiac geometry.

2. A method for reducing regurgitation of an atrioventricular valve of a heart, comprising: delivering a material through an external portion of muscle wall of the heart and into a muscle wall region of the heart proximate the papillary muscle, the material displacing a portion of said muscle wall region inward and toward the center line of the ventricular cavity of the heart so as to normalize papillary muscle geometry and improve leaflet coaptation.

3. The method of claim 1 or 2, wherein the delivering step further comprises the step of injecting the material.

4. The method of claim 1 or 2, wherein the muscle wall region comprises the tissue plane between the coronary sinus and mitral annulus in the heart.

5. The method of claim 1 or 2, wherein the muscle wall region comprises a portion of the base of the heart.

6. The method of claim 1 or 2, wherein the muscle wall region includes damaged tissue.

7. The method of claim 1 or 2, wherein the delivering step further includes the step of: imaging the muscle wall region with ultrasound.

8. The method of claim 1 or 2, wherein the material retains a predetermined shape and volume after delivery.

9. The method of claim 1 or 2, wherein the material comprises a nickel titanium alloy.

10. The method of claim 1 or 2, wherein the material comprises a hydrogel that stiffens near body temperature.

11. The method of claim 1 or 2, wherein the material is encapsulated in a structure.

12. The method of claim 11, wherein the structure is a balloon.

13. The method of claim 11, wherein the structure is a cellular matrix comprised of fibroblasts.

14. The method of claim 1 or 2, wherein the material is engineered cellular tissue.

15. The method of claim 14, wherein the cellular tissue is delivered with a biodegradable scaffolding network.

16. The method of claim 14, wherein the cellular tissue comprises stem cells.

17. The method of claim 14, wherein the cellular tissue comprises myocytes producing dynamic contraction in temporal coordination with electrical activation of the heart.

18. The method of claim 1 or 2, wherein the material comprises conductive polymers, and the material displaces the portion of the muscle wall region by contracting in response to electrical triggering.

19. The method of claim 1 or 2, wherein the delivering step comprises an invasive cardiac procedure.

20. The method of claim 1 or 2, wherein the delivering step comprises a thoracoscopic procedure.

21. The method of claim 1 or 2, wherein the delivering step serves to reduce mitral annulus size.

22. The method of claim 1 or 2, further comprising the step of: repeating the delivering step at a different muscle wall region of the heart.

* * * * *